(12) United States Patent
Stopp et al.

(10) Patent No.: US 11,864,955 B2
(45) Date of Patent: Jan. 9, 2024

(54) VIDEO BASED MICROSCOPE ADJUSTMENT

(71) Applicant: Brainlab AG, Munich (DE)

(72) Inventors: Sebastian Stopp, Munich (DE); Johannes Manus, Munich (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 17/880,914

(22) Filed: Aug. 4, 2022

(65) Prior Publication Data

US 2023/0054305 A1 Feb. 23, 2023

Related U.S. Application Data

(63) Continuation of application No. 16/629,351, filed as application No. PCT/EP2018/068818 on Jul. 11, 2018, now Pat. No. 11,471,241.

(30) Foreign Application Priority Data

Aug. 11, 2017 (WO) .................. PCT/EP2017/070487

(51) Int. Cl.
*G02B 27/00* (2006.01)
*A61B 90/25* (2016.01)
(Continued)

(52) U.S. Cl.
CPC .............. *A61B 90/25* (2016.02); *A61B 17/00* (2013.01); *A61B 34/20* (2016.02); *A61B 90/361* (2016.02);
(Continued)

(58) Field of Classification Search
CPC ......... A61B 90/25; A61B 17/00; A61B 34/20; A61B 90/361; A61B 2017/00203;
(Continued)

(56) References Cited

U.S. PATENT DOCUMENTS

| 4,574,199 A | 3/1986 | Pryor |
| 5,243,665 A | 9/1993 | Maney et al. |

(Continued)

FOREIGN PATENT DOCUMENTS

| DE | 102016100566 A1 | 7/2017 |
| EP | 3025666 A1 | 6/2016 |
| EP | 3285107 A1 | 2/2018 |

OTHER PUBLICATIONS

International Search Report and Written Opinion for corresponding international application No. PCT/EP2018/068818, dated Oct. 22, 2018. 15 Pages.

(Continued)

*Primary Examiner* — Frank F Huang
(74) *Attorney, Agent, or Firm* — Tucker Ellis LLP

(57) ABSTRACT

The present disclosure relates to an optical observation device which is controlled in a sterility preserving manner, and to a corresponding controlling program and/or program storage medium. The optical observation device includes a main structure having at least one optical camera, a support structure adapted to variably position the main structure, and a control unit that receives a sequence of images from the at least one optical camera, searches a current image from the sequence of images for a trackable object, tracks the trackable object shown in the sequence of images subsequent to the current image; and controls adjustable properties of AR-content superimposed with the sequence of images in accordance with a motion of the trackable object, wherein the adjustable properties of the AR-content include a location, orientation, and/or size of the AR-content with respect to the sequence of images.

20 Claims, 1 Drawing Sheet

(51) Int. Cl.
  *A61B 34/20*   (2016.01)
  *A61B 90/00*   (2016.01)
  *A61B 17/00*   (2006.01)
  *G02B 27/01*   (2006.01)
(52) U.S. Cl.
  CPC .. *G02B 27/017* (2013.01); *A61B 2017/00203* (2013.01); *A61B 2017/00207* (2013.01); *A61B 2017/00973* (2013.01); *A61B 2034/2057* (2016.02); *A61B 2034/2065* (2016.02); *A61B 2034/2068* (2016.02)
(58) Field of Classification Search
  CPC ........... A61B 2017/00207; A61B 2017/00973; A61B 2034/2057; A61B 2034/2065; A61B 2034/2068; A61B 90/20; A61B 2034/2055; G02B 27/017; G02B 7/001; G02B 21/0012
  See application file for complete search history.

(56) References Cited

U.S. PATENT DOCUMENTS

| | | |
|---|---|---|
| 5,345,087 A | 9/1994 | Luber |
| 5,749,362 A | 5/1998 | Funda |
| 5,920,394 A | 7/1999 | Gelbert et al. |
| 6,175,642 B1 | 1/2001 | Gobbi |
| 8,535,336 B2 | 9/2013 | Trovato |
| 10,646,156 B1 | 5/2020 | Schnorr |
| 10,883,708 B2 | 1/2021 | Chien |
| 2005/0063047 A1 | 3/2005 | Obrebski |
| 2008/0185430 A1 | 8/2008 | Goldbach |
| 2008/0262312 A1 | 10/2008 | Carroll et al. |
| 2009/0088634 A1 | 4/2009 | Zhao et al. |
| 2014/0207541 A1 | 7/2014 | Nerayoff et al. |
| 2015/0173846 A1 | 6/2015 | Schneider et al. |
| 2016/0331584 A1 | 11/2016 | Ren |
| 2019/0293935 A1 | 9/2019 | Schneider et al. |
| 2020/0138518 A1* | 5/2020 | Lang ........................ A61B 5/05 |
| 2021/0137632 A1* | 5/2021 | Stopp ................... G02B 27/017 |
| 2021/0137634 A1* | 5/2021 | Lang ..................... A61B 90/13 |
| 2021/0192759 A1* | 6/2021 | Lang ........................ G06T 3/40 |

OTHER PUBLICATIONS

1 Beyond Auto Tracker Camera, http://1beyond.com/autotracker, retreived from the internet on Jul. 14, 2017. 5 pages.

SOLOSHOT Robot Camerman, https://soloshot.com/, retrieved from the Internet on Jul. 14, 2017. 12 pages.

* cited by examiner

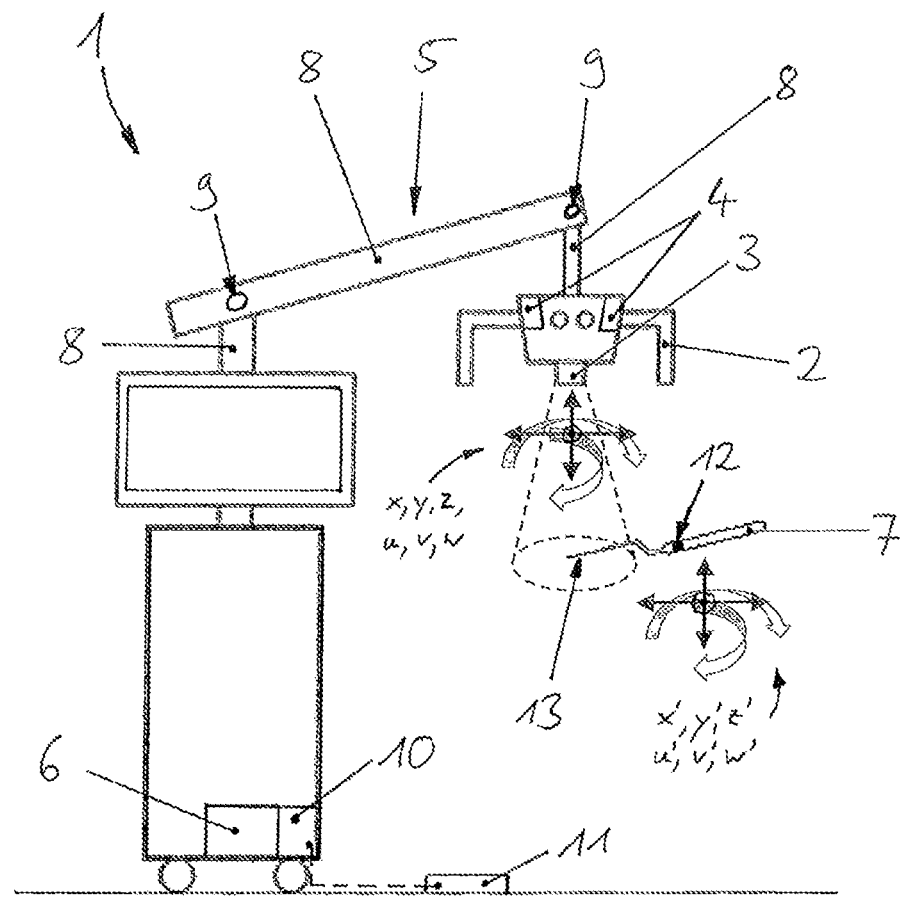

VIDEO BASED MICROSCOPE ADJUSTMENT

RELATED APPLICATION DATA

This application is a continuation of U.S. patent application Ser. No. 16/629,351, filed on Jan. 8, 2020, which is a national phase application of International Application No. PCT/EP2018/068818, filed on Jul. 11, 2018, which claims priority to International Application No. PCT/EP2017/070487, filed on Aug. 11, 2017, all of which are incorporated herein by reference in their entirety.

TECHNICAL FIELD

The present invention relates to an optical observation device which is adjusted in a sterility preserving manner by utilizing a hand-held device within the field of view of the observation device. The present invention further relates to a corresponding computer program run on an observation device controller for adjusting such observation device.

BACKGROUND

During medical procedures optical observations devices such as microscopes or robotic arms with cameras attached to it may be utilized in order to help surgical personnel to see small anatomical details of a patient to be treated. In this context it is often necessary to readjust the optical observation device in order to look at one or even more details of interest from different positions. It may be even necessary to move the whole observation device out of the working area for particular steps of a medical workflow and to reposition the observation device thereafter, preferably at the same position. Moreover, it is desirable to enable a plurality of persons to use the observation device, which requires a positional rearrangement, as well. Currently, optical observation devices such as microscopes are adjusted manually, for example by simply grasping handles of the device and by pressing a button to release the break of an articulated support arm which is otherwise holding the device rigidly in place.

Other solutions make use of remote controls or foot pedals for controlling the device. Fully automatic controls for positioning microscopes are also known in the art, which however, prevent personnel to make adjustments by their own desire.

SUMMARY

The present invention provides an optical observation device which can be easily controlled by medical personnel by their own desire and initiative, and even in a sterility preserving manner.

The optical observation device of the present invention comprises:
a) a main structure comprising at least one optical camera;
b) a motorized support structure adapted to variably position the main structure at or near a workplace to be observed; and
c) a control unit adapted to perform the following procedural steps:
receive a sequence of images from the at least one optical camera;
search a current image from the sequence of images for a trackable object and track the trackable object shown in the sequence of images subsequent to the current image;
receive a trigger signal for controlling the motorized support structure, an optical set-up and/or the at least one optical camera in accordance with a motion of the trackable object.

In other words, of the inventive observation device has, as a main structure, a microscope or a camera adapted to be aimed at an object or a patient to be treated and to provide a sequence of images thereof. The sequence of images may form a video. In order to hold the microscope or camera in place in or next to the object or the anatomical structure of a patient to be observed, a support structure is provided which may be connected at one end to the ceiling or a wall of a room, but may also be connected to a mobile trolley. At its other end, the support structure holds the microscope or camera in a positionally fixed but yet adjustable position with respect to its first end and, since the patient is immobilized within the room as well, with respect to the object or the anatomical structure of the patient. Thus, the relative position between the main structure and the observed object or anatomy remains unchanged until a user such as medical personnel decides otherwise.

For this case one specific embodiment of the inventive observation device comprises a control unit that causes the support structure to move the main structure. For this purpose the control unit receives a video from a camera of the main structure and searches this video for an image of a specific trackable and hand-held device that is utilized for controlling the observation device. As soon as the control unit receives a signal indicating that personnel wishes the main structure to move in accordance with the hand-held device, the control units sends control signals to the support structure, for example to one or more motors of the support structure such that the main structure is eventually moved in accordance with the motion of the hand-held device.

Additionally or alternatively to this motion-control and in accordance with another specific embodiment of the present invention, the control unit may send control signals to an optical set-up and/or to the at least one optical camera of the main structure so as to adjust certain properties such as the zoom factor or the focus of the optical set-up or the optical camera in accordance with the motion of the hand-held device.

In summary, the inventive optical observation device can be adjusted in various ways simply by moving a hand-held device within the field of view of a microscope or an optical camera of the observation device. Since this does not require any physical interaction with the observation device, the present invention not only allows for an intuitive and therefore simple possibility to control a medical microscope or camera, but also helps in preserving sterility during an entire medical workflow.

In accordance with another embodiment of the present invention and already indicated further above, the main structure may comprise or be a surgical microscope as used during a medical workflow for treating a patient. However, the present invention may also be utilized for any other workflow apart from medical workflows, for which a touchless control of an optical observation device is desired.

In accordance with a further embodiment of the present invention the control unit is adapted to receive the trigger signal via a sterility preserving user interface, particularly via covering or uncovering an optically recognizable feature provided on the trackable object, via a foot pedal switch, via voice command and/or via gestures which are recognizable from the sequence of images. For example, a predefined motion of the hand-held device may be recognized in the video images. For example, turning the device around its longitudinal axis or rotating one end of the device in a circular manner with the other end of the device being positionally fixed may be recognized as a triggering gesture. As often used during medical procedures, optically recognizable markers (such as a marker spheres) or other designated optionally recognizable features may be provided on the instrument, which may also be recognized by a medical tracking system associated with a medical navigation system for calculating the spatial position of the instrument, may be temporarily covered by the user so as to provoke a triggering signal.

According to another embodiment of the invention, the motion of the main structure, but also the adjustable properties of the optical set-up and/or optical camera, may be coupled to the motion of the trackable object via at least one, particularly selectable conversion factor. Such conversion factor may cause the motion of the main structure to be amplified or to be reduced and/or to be damped as compared to the motion of the trackable object. By doing so, moving the hand-held device by a larger distance will result in a respective adjustment of, for example, the position and/or the focus length by a smaller or even larger distance as compared to the distance covered by the hand-held device. For obtaining a "smoother", less "nervous" adjustment of the observation device, a damping factor may be interposed between the motion of the hand-held device and the controlled adjustment.

Further, it is conceivable that an upper threshold for the speed of motion of the hand-held device is defined such that motions above the threshold are ignored. By doing so, abrupt or accidental and undesired motions will not result in also undesired adjustment of the observation device.

According to another embodiment of the present invention at least two degrees of freedom for the motion of the main structure are controlled separately, such that motion of the main structure in at least one of the at least two degrees of freedom is blocked while the main structure is controlled to move within at least one other of the at least two degrees of freedom. Thus, an adjustment is performed only in certain degrees of freedom which reduces the amount of undesired adjustment. For example a substantially vertical motion of the hand-held device will cause an adjustment in a vertical direction, while any other degrees of freedom for the adjustment are blocked. Thus, an "inaccurate" control input with a, in this case, slight horizontal deviation cannot lead to an unintended adjustment in a horizontal direction. In this context it is to be noted that adjustments can in principle be performed in all six degrees of freedom, three translational degrees of freedom and three rotational degrees of freedom. Of course, measures will have to be provided that enable the user to "switch" between the plurality of degrees of freedom for respective adjustments.

In addition to the above described adjustments of the properties of the optical observation device itself including, for example, the spatial position, the zoom factor and the focus length, the present invention may also provide for further adjustments including the adjustment of properties of AR-content superimposed with the sequence of images, particularly the location, orientation and/or size of AR-content with respect to the sequence of images; in accordance with a motion of the hand-held device.

Controlling the properties of AR content superimposed with the sequence of images, particularly the location, orientation and/or size of AR content with respect to the sequence of images in accordance with a motion of the trackable object as described above may even be considered as a separate invention without and independent of controlling the motorized support structure, the optical set-up and/or the at least one optical camera.

As already indicated further above, the trackable object may be a hand-held device or hand-held medical instrument, particularly a pointer instrument as often utilized in medical procedures. Further, the hand-held device may be provided as a disposable device.

The hand-held device may be recognized on the video images via a ring pattern provided on the hand-held device, particularly the tip thereof.

A further aspect of the present invention relates to a program, which when running on a processor of the control unit described above, causes the processor to perform the above described procedural steps. An even further aspect of the present invention relates to a program storage medium on which such program is stored, in particular in a non-transitory form.

The system and the program system are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

Definitions

The procedure performed in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

The invention also relates to a navigation system for computer-assisted surgery, comprising: the computer of the preceding claim, for processing the absolute point data and the relative point data;

a detection device for detecting the position of the main and auxiliary points in order to generate the absolute point data and to supply the absolute point data to the computer;

a data interface for receiving the relative point data and for supplying the relative point data to the computer; and a user interface for receiving data from the computer in order to provide information to the user, wherein the received data are generated by the computer on the basis of the results of the processing performed by the computer.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows determining the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

A pointer is a rod which comprises one or more—advantageously, two—markers fastened to it and which can be used to measure off individual co-ordinates, for example spatial co-ordinates (i.e. three-dimensional co-ordinates), on a part of the body, wherein a user guides the pointer (for example, a part of the pointer which has a defined and advantageously fixed position with respect to the at least one marker attached to the pointer) to the position corresponding to the co-ordinates, such that the position of the pointer can be determined by using a surgical navigation system to detect the marker on the pointer. The relative location between the markers of the pointer and the part of the pointer used to measure off co-ordinates (for example, the tip of the pointer) is for example known. The surgical navigation system then enables the location (of the three-dimensional co-ordinates) to be assigned to a predetermined body structure, wherein the assignment can be made automatically or by user intervention.

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

BRIEF DESCRIPTION OF DRAWINGS

In the following, the invention is described with reference to the enclosed FIGURE which represents a preferred embodiment of the invention. The scope of the invention is however not limited to the specific features disclosed in the FIGURE, which shows:

FIG. 1 an optical observation device in accordance with the present invention controlled via a hand-held pointer instrument.

DETAILED DESCRIPTION

The optical observation device 1 shown in FIG. 1 comprises, as a main structure, a surgical microscope 2 which is held above a workplace by an articulated support structure 5 which is, at its other end, connected to a mobile wheel trolley.

The spatial position of the microscope 2 with respect to the trolley and therefore also with respect to the workplace is adjusted by activating motorized joints 9 between the arm sections 8 of the articulated support arm 5.

In accordance with the present invention, this is done with the help of a pointer instrument 7 which is positioned within the field of view of the microscope. By covering an optically detectable feature 12 on the instrument 7 (which has to be at this time within the microscope's field of view and may be a colored spot or marking; even tracking markers or one or more rings of the ring pattern 13 may act as the feature 12) or by pushing the foot pedal switch 11 which is connected to an interface 10 of the control unit 6, a triggering signal is provoked that sets off the following control procedure:

The spatial position of a ring pattern 13 which is provided at the tip of the instrument 7 is determined within the sequence of images the control unit 6 receives from the cameras 4 of the microscope 2. As soon as the instrument 7 is moved by a user within the field of view of the microscope, the control unit 6 controls the motorized joints 9 such that the microscope 2 "follows" the ring pattern 13 on the instrument 7. Since "exaggerated" microscope motions are undesired, the microscope 2 will move by a smaller distance than the instrument 7 does. Obviously, the ring-pattern 13 is not suitable for controlling the microscope 2 in accordance with a rotation of the instrument 7 around its longitudinal axis. However, other features recognizable for the cameras 4 or even for an external medical tracking system may be provided to allow for tracking this motion as well. Provided that all six degrees of freedom (x', y', z', u', v', w') are recognized within the field of view of the microscope 2, the position of the microscope 2 can in principle be adjusted in six degrees of freedom (x, y, z, u, v, w). Even though the above lines describe a positional adjustment of the microscope 2 with respect to a medical workplace underneath the microscope 2, the properties of an optical set-up 3 of the microscope 2 or the cameras 4 of the microscope 2 may alternatively or additionally be adjusted via a motion of the instrument 7 in the same manner as described above. For example, the focal length of the optical set-up 3 of the microscope 2 may be adjusted by moving the instrument 7 in a vertical direction. In a further example, the zoom factor of the microscope cameras 4 may be adjusted by moving the instrument 7 in a horizontal or even in a vertical direction.

The invention claimed is:

1. An optical observation device comprising:
a main structure comprising a surgical microscope having at least one optical camera adapted to be aimed at a patient to be treated;
a support structure adapted to variably position the main structure at or near a workplace to be observed; and
a control unit adapted to:
receive a sequence of images from the at least one optical camera;
search a current image from the sequence of images for a trackable object positioned within a field of view of the at least one optical camera;
track the trackable object shown in the sequence of images subsequent to the current image; and
control properties of AR-content superimposed with the sequence of images in accordance with a motion of the trackable object, the properties of the AR-content being controlled by the motion of the trackable object within the field of view of the at least one optical camera, the properties of the AR-content including a location, orientation, and/or size of the AR-content with respect to the sequence of images.

2. The optical observation device according to claim 1, wherein the control unit is further adapted to control properties of an optical set-up including a focus-point of the optical set-up and/or to control properties of the at least one optical camera including a zoom-factor of the at least one optical camera in accordance with the motion of the trackable object.

3. The optical observation device according to claim 1, wherein an upper threshold for a speed of motion of the trackable object is defined and motions above the upper threshold are ignored.

4. The optical observation device of claim 1, wherein a handheld medical instrument is recognized as the trackable object, which is provided as a disposable device.

5. The optical observation device according to claim 4, wherein the medical instrument is tracked via a ring pattern provided on the medical instrument and visible in the sequence of images.

6. The optical observation device of claim 1, wherein the support structure is a motorized support structure and the control unit is further adapted to control the motorized support structure, an optical set-up and/or the at least one optical camera, wherein motion of the main structure, and/or adjustable properties of the optical set-up and/or of the at least one optical camera, is coupled to the motion of the trackable object via at least one conversion factor.

7. The optical observation device according to claim 6, wherein at least two degrees of freedom for the motion of the main structure are controlled separately, such that motion of the main structure in at least one of the at least two degrees of freedom is blocked while the main structure is controlled to move within at least one other of the at least two degrees of freedom.

8. The optical observation device according to claim 6, wherein the control unit is adapted to receive a trigger signal for controlling the motorized support structure, the optical set-up and/or the at least one optical camera, in accordance with the motion of the trackable object, via a sterility preserving user interface, via covering or uncovering an optically recognizable feature provided on the trackable object, wherein the trigger signal is activated by a foot pedal switch, voice command, and/or gestures which are recognizable from the sequence of images.

9. The optical observation device according to claim 6, wherein the motorized support structure is controlled to move the main structure in accordance with the motion of the trackable object, wherein the motorized support structure is an articulated arm with at least two arm sections which are hingedly connected to each other via at least one motorized joint.

10. The optical observation device according to claim 9, wherein the motion of the main structure is coupled to the motion of the trackable object via the at least one conversion factor causing:
- the motion of the main structure to be amplified as compared to the motion of the trackable object;
- the motion of the main structure to be reduced as compared to the motion of the trackable object; and/or
- the motion of the main structure to be damped as compared to the motion of the trackable object.

11. An optical observation device comprising:
- a main structure comprising at least one optical camera adapted to transmit a sequence of images;
- a support structure adapted to move the main structure; and
- a control unit adapted to receive the sequence of images from the at least one optical camera, track a trackable object shown in the sequence of images, and control properties of AR-content superimposed with the sequence of images in accordance with a motion of the trackable object, the properties of the AR-content being controlled by the motion of the trackable object within a field of view of the at least one optical camera, wherein the properties of the AR-content include a location, orientation, and/or size of the AR-content with respect to the sequence of images.

12. The optical observation device according to claim 11, wherein the control unit is further adapted to search a current image from the sequence of images for the trackable object after receipt of the sequence of images.

13. The optical observation device according to claim 12, wherein the support structure is a motorized support structure and the control unit is further adapted to transmit a signal to the motorized support structure of where to move the main structure in accordance with the motion of the trackable object via at least one conversion factor, wherein the control unit is further adapted to receive a trigger signal for controlling the motorized support structure in accordance with the motion of the trackable object.

14. The optical observation device according to claim 13, wherein the motion of the main structure is coupled to the motion of the trackable object via the at least one conversion factor causing the motion of the main structure to be reduced as compared to the motion of the trackable object, and/or the motion of the main structure to be damped as compared to the motion of the trackable object.

15. The optical observation device according to claim 11, wherein the control unit is further adapted to control properties of an optical set-up including a focus-point of the optical set-up and/or to control properties of the at least one optical camera including a zoom-factor of the at least one optical camera in accordance with the motion of the trackable object.

16. The optical observation device according to claim 11, wherein the support structure is a motorized support structure and the control unit is further adapted to transmit a signal to the motorized support structure of where to move the main structure in accordance with the motion of the trackable object via at least one conversion factor.

17. The optical observation device according to claim 16, wherein the motorized support structure is controlled to move the main structure in accordance with the motion of the trackable object, and wherein the motorized support structure is an articulated arm with at least two arm sections which are hingedly connected to each other via at least one motorized joint.

18. The optical observation device according to claim 16, wherein the control unit is adapted to receive a trigger signal for controlling the motorized support structure, via a sterility preserving user interface, via covering or uncovering an optically recognizable feature provided on the trackable object, wherein the trigger signal is activated by a foot pedal switch, voice command, and/or gestures which are recognizable from the sequence of images.

19. The optical observation device according to claim 18, wherein covering a designated feature of the trackable object, which is visible to the at least one optical camera is recognized as a gesture provoking the trigger signal.

20. A non-transitory computer readable storage medium storing a program, that when executed on at least one processor of a computer or loaded onto the at least one processor of the computer, causes the computer to:
- receive a sequence of images from at least one optical camera;
- search a current image from a sequence of images for a trackable object;
- track the trackable object shown in the sequence of images subsequent to the current image; and
- control adjustable properties of AR-content superimposed with the sequence of images, adjustable properties of an optical set-up, and/or adjustable properties of the at least one optical camera in accordance with motion of the trackable object, the adjustable properties of the AR-content being controlled by the motion of the trackable object within the field of view of the at least one optical camera,
wherein the adjustable properties of the AR-content include a location, orientation, and/or size of the AR-content with respect to the sequence of images.

* * * * *